(12) United States Patent
Bosworth

(10) Patent No.: US 8,909,327 B1
(45) Date of Patent: Dec. 9, 2014

(54) INSTRUMENT AND METHOD FOR DIAGNOSING DRY EYE IN A PATIENT

(75) Inventor: Charles Bosworth, Oceanside, CA (US)

(73) Assignee: Allergan, Inc., Irvine, CA (US)

( * ) Notice: Subject to any disclaimer, the term of this patent is extended or adjusted under 35 U.S.C. 154(b) by 547 days.

(21) Appl. No.: 13/167,099

(22) Filed: Jun. 23, 2011

Related U.S. Application Data (60) Provisional application No. 61/357,932, filed on Jun. 23, 2010.

(51) Int. Cl.
A61B 5/00 (2006.01)

(52) U.S. Cl.
USPC .......................................... 600/473; 600/476

(58) Field of Classification Search
USPC ................................................ 600/473, 476
See application file for complete search history.

(56) References Cited

U.S. PATENT DOCUMENTS

| | | | |
|---|---|---|---|
| 5,943,117 A | | 8/1999 | Van de Velde |
| 7,121,666 B2 * | | 10/2006 | Tseng et al. .................. 351/206 |
| 7,771,353 B2 | | 8/2010 | Luce |
| 2004/0189938 A1 | | 9/2004 | Eagan |
| 2007/0211214 A1 | | 9/2007 | Dai |
| 2008/0281304 A1 | | 11/2008 | Campbell |
| 2009/0059163 A1 | | 3/2009 | Pinto |
| 2009/0153738 A1 | | 6/2009 | Allred et al. |
| 2009/0231546 A1 | | 9/2009 | Dai |
| 2010/0039614 A1 | | 2/2010 | Morris et al. |
| 2010/0110379 A1 | | 5/2010 | Zhou et al. |
| 2010/0123874 A1 | | 5/2010 | Allred et al. |
| 2010/0195876 A1 | | 8/2010 | Artal Soriano et al. |
| 2010/0201944 A1 | | 8/2010 | Lewis et al. |
| 2010/0249532 A1 * | | 9/2010 | Maddess et al. ............... 600/300 |
| 2011/0134391 A1 | | 6/2011 | Dai et al. |

OTHER PUBLICATIONS

Artal et al., Odd aberrations and double-pass measurements of retinal image quality, (1995) *J. Opt. Soc. Am. A.* 12:195-201.

Artal et al., *Optical Modulation Transfer and Contrast Sensitivity with Decentered Small Pupils in the Human Eye*, (1996) Vision Res. vol. 36, No. 22, pp. 3575-3586, 1996.

Frisen, High-pass resolution perimetry, (1993) *Documenta Ophthalmologica* 83:1-25.

Goldberg, *Visiometrics' Optical Quality Analysis System, The OQAS is a diagnostic tool that objectively analyzes total quality of vision.* 2006.

Himebaugh et al, *Use of Retroillumination to Visualize Optical Aberrations Caused by Tear Film Break-Up*, Optometry and Vision Science, vol. 80, No. 1, Jan. 2003.

Lombardo et al., Wave aberration of human eyes and new descriptors of image optical quality and visual performance, (2010) *J. Cataract Refract Surg* 36:313-331.

(Continued)

*Primary Examiner* — Peter Luong (74) *Attorney, Agent, or Firm* — Barbara C. Potts (57) ABSTRACT

The present invention relates to an instrument and method for measuring the optical quality of an eye in a human subject. The instrument, which can be of either a single or double pass design and may include three-separate channels, permits real-time, simultaneous measurement of optical aberrations in the eye, retro-illumination of tear film to assess tear film stability, and scoring of psychophysical measures of visual performance. The simultaneous measurement of these parameters of optical quality and visual performance with the present instrument enables the operator to more accurately assess conditions and diseases of the eye, including dry eye disease (DED).

18 Claims, 2 Drawing Sheets

(56) References Cited

OTHER PUBLICATIONS

Thibos, Principle of Hartmann-Shack Aberrometry, *Journal of Refractive Surgery*, vol. 16, S563-S565, 2000.
Himebaugh et al, *Use of Retroillumination to Visualize Optical Aberrations Caused by Tear Film Break-Up*, Optometry and Vision Science, vol. 80, No. 1, Jan. 2003, pp. 69-78.
Albarran C, Pons AM, Lorente A, Montes-Mico R, Artigas JM. Influence of the tear film on optical quality of the eye. Contact Lens Ant Eye. 1997;20:129-135.
Beer DR, MacLeod DIA, Miller TP. The Extended Maxwellian View (BIGMAX): A high-intensity, high-saturation color display for clinical diagnosis and vision research. Behavior Research Methods. 2005; 37: 513-521.
Begley CG, Chalmers RL, Mitchell GL, et al. Characterization of ocular surface symptoms from optometric practices in North America. Cornea 2001;20:610-618.
Chen JJ, Rao K, Pflugfelder SC. Corneal Epithelial Opacity in Dysfunctional Tear Syndrome. Am J Ophthalmol 2009;148:376-382.
Díaz-Doutón F, Benito A, Pujol J, Arjona M, Güell JL, and Artal P. Comparison of the Retinal Image Quality with a Hartmann-Shack Wavefront Sensor and a Double-Pass Instrument. Invest Ophthalmol Vis Sci. 2006;47:1710-1716.
Frisen L. A computer-graphics visual field screener using high-pass spatial frequency resolution targets and multiple feedback devices. Doc Ophthalmol Proc Ser.1987;49:441-446.
Goto E, Yagi Y, Matsumoto Y, Tsubota K. Impaired Functional Visual Acuity of Dry Eye Patients. Am J Ophthalmol. 2002;133:181-186.
Howland B, Ginsburg A, Campbell F. High-pass spatial frequency letters as clinical optotypes. Vision Res 1978;18:1063-6.
Johnson CA, Chauhan BC, Shapiro LR. Properties of Staircase Procedures for Estimating Thresholds in Automated Perimetry. Invest Ophthalmol Vis Sci 1992;33:2966-2974.
Koh S, Maeda N, Kuroda T, et al. Effect of tear film break-up on higher-order aberrations measured with wavefront sensor. Am J Ophthalmol. 2002;134:115-117.
Koh S, Maeda N, Hirohara Y, Mihashi T, Bessho K, Hori Y, Inoue T., Watanabe H, Fujikado T and Tano Y. Serial Measurements of Higher-Order Aberrations after Blinking in Patients with Dry Eye. Invest Ophthalmol Vis Sci. 2008; 49:133-138.
Liu H, Thibos L, Begley CG, and Bradley A. Measurement of the time course of optical quality and visual deterioration during tear break-up. Invest Ophthalmol Vis Sci. 2010;51:3318-3326.

Martinez GA, Sample PA, Weinreb RN. Comparison of high-pass resolution perimetry and standard automated perimetry in glaucoma. Am J Ophthalmol.1995; 119:195-201.
Montes-Mico R, Alio JL, Charman N. Postblink changes in the ocular modulation transfer function measured by a double-pass method. J Cataract Refract Surg. 2004;30:1649-1652.
Montés-Micó R, Caliz A, Alio JL. Changes in ocular aberrations after artificial tears instillation in dry eye patients. Invest Ophthalmol Vis Sci. 2005; 46:4468-4473.
Montés-Micó R, Phil M. Role of the tear film in the optical of the human eye. J Cataract Refract Surg 2007; 33: 1631-1635.
Nichols KK, Begley CG, Caffery B, Jones LA. Symptoms of ocular irritation in patients diagnosed with dry eye. Optom Vis Sci 1999;76:838-844.
Ridder WH, J LaMotte, Hall JQ, Sinn R, Nguyenm AL, Abufarie L. Contrast Sensitivity and Tear Layer Aberrometry in Dry Eye Patients. Optom Vis Sci 2009;86:E1059-E1068.
Solomon JA and Pelli DG. The visual filter mediating letter identification. Nature. 2004: 369: 395-398.
Sade de Paiva C, Lindsey JL, Pflugfelder SC. Assessing the severity of keratitis sicca with videokeratoscopic indices. Ophthalmology 2003;110:1102-1109.
Sample PA, Ahn DS, Lee PC, Weinreb RN. High-pass resolution perimetry in eyes with ocular hypertension and primary open-angle glaucoma. Am J Ophthalmol. 1992;113:309-316.
Thibos LN, Hong X. Clinical applications of the Shack-Hartmann aberrometer. Optom Vis Sci 1999;76:817-825.
Tutt R, Bradley A, Begley C, Thibos LN. Optical and visual impact of tear break-up in human eyes. Invest Ophthalmol Vis Sci. 2000;41:4117-4123.
Westheimer, G. (1966). The Maxwellian view. Vision Research, 6,669-682.
Zhuang H, Zhou X, and Xu J. A Novel Method for Pachymetry Mapping of Human Precorneal Tear Film Using Pentacam with Fluorescein. (Invest Ophthalmol Vis Sci. 2010;51:156-159.
Iester et al, "Correlation of Relative Dispersion Analysis and Other High Pass Resolution Perimetry Indices with Standard Threshold Perimetry", Proceedings of the XIIIth International Perimetric Society Meeting, 1998/1999, pp. 301-305.
OQAS™II, Visiometrics User's Manual, Version 5.2 (English), Sep. 2009, Printed in Spain, 53 pages.

* cited by examiner

Fig. 1

High-pass Resolution Perimetry (HRP) test target

Fig. 2

High-pass Resolution Perimetry (HRP) test target sizes

Fig. 3

INSTRUMENT AND METHOD FOR DIAGNOSING DRY EYE IN A PATIENT

CROSS-REFERENCE TO RELATED APPLICATIONS

This Application claims the benefit of U.S. Provisional Application 61/357,932, filed Jun. 23, 2010, which is hereby incorporated by reference.

BACKGROUND AND SUMMARY OF THE INVENTION

The present invention relates to an instrument and method for measuring the optical quality of an eye in a human subject. The instrument, which can be of either a single or double pass design and may include three-separate channels, permits real-time, simultaneous measurement of optical aberrations in the eye, retro-illumination of tear film to assess tear film stability, and visual performance. Tear film instability and optical aberrations can affect the optical quality and, consequently, the visual performance of the eye. By monitoring tear film stability and optical aberrations simultaneously in real time with visual performance, an operator may use the present instrument to more accurately assess conditions and diseases of the eye, including dry eye disease (DED) in a human subject.

The International Dry Eye Workshop (DEWS) defined Dry Eye Disease (DED) as a multifactorial disease of the tears and ocular surface that results in symptoms of discomfort, visual disturbance, and tear film instability with potential damage to the ocular surface. It is accompanied by increased osmolarity of the tear film and inflammation of the ocular surface (DEWS 2007). Irritative symptoms are largely responsible for the public health burden and for the care-seeking behavior of dry eye patients and their desire for therapy. Notably, dry eye patients commonly complain of transiently blurred vision that temporarily clears with a blink (Nichols et al, 1999; Begley et al 2001; Sade de Paiva et al 2003).

The prevalence of dry eye ranges from about 5% to over 35% across large epidemiological studies (DEWS 2007). The large variance in the reported prevalence rates originates from the heterogeneity of the diseases currently classified as DED and the fact that no single diagnostic test can be performed in the clinic to reliably distinguish individuals with DED from those without DED. Instead, a battery of tests are routinely employed which can be broken into symptom questionnaires, grading of ocular surface staining, measures of tear film stability, measures of tear flow, and measures of tear composition. The combination of tests is burdensome for both patients and physicians as these tests currently rely upon physician/patient interaction for reliable collection and interpretation. For example, currently an ophthalmologist may conduct an ocular surface exam which includes tear breakup with fluorescein, surface staining assessment with fuorescein/yellow filter, a Schirmer I test without anesthetic, and lid and meibomian morphology to test for dry eye.

Accordingly, dry eye disease is typically diagnosed in view of the patient's symptoms considered together with the results of the tests ophthalmologists perform (e.g., tear film stability and tear flow). While numerous symptom questionnaires exist with varying degrees of validation, the Ocular Surface Disease Index (OSDI) is the most widely utilized. Tear film stability is commonly measured by determining the Tear Film Break-Up Time (TFBUT). A standard volume of fluorescein dye is applied to the eye, the patient is allowed to blink and the time between the blink and the first appearance of a dark spot is recorded as the tear break-up time. Reflex tear flow is measured using the Schirmer test. It is accepted that the wide intrasubject variation on these tests is influenced by both day-to-day and visit to-visit fluctuation. It must also be recognized that there is wide intrasubject variation with regard to the impact of tear film stability between blinks (i.e., some patients may experience tear film break-up before their next blink). This source of variability is often used to explain why some dry eye disease patients complain of "transiently" blurred vision. To eliminate between blink variability across tests, tear film break-up must be measured both objectively and subjectively at the same time. Unfortunately, no standard instrument exists which can simultaneously measure tear break-up both objectively and subjectively.

Consistent with clinical practice, the DEWS sub-committee on clinical trial design recommended that the following endpoints be included in clinical drug trials: 1) An objective measure of visual function (e.g., Functional Visual Acuity); 2) Determination of tear volume and production (e.g., Schirmer test or fuorescein dilution test); 3) Determination of tear stability (e.g., tear breakup with fuorescein or a non-invasive tear breakup device such as videokeratography); 4) Measurement of tear composition (e.g., osmolarity, determination of specific protein content, or the measurement of inflammatory mediators in tears); and 5) Measurement of ocular surface integrity.

Of these suggested measures the need for an objective and reliable measure of visual function has yet to be satisfied. Three requirements should be met to optimally and non-invasively measure the relationship between tear stability, aberrations, and functional outcomes: 1) measurements should be performed without anesthesia, pupil dilation or the instillation of dyes (e.g., fluorescein) (see Koh et al, 2008); 2) visual testing for tear film irregularities is time sensitive and stimuli should be presented relative to a patient's blink; and 3) all measurements should be performed simultaneously using a stimulus which is optimally sensitive to tear film induced aberrations (see Liu et al, 2010).

Recognizing the difficulty of measuring visual function within a blink interval the scientific advancement has instead focused upon the real time measurement of optical aberrations as a surrogate for functional loss. Indeed, several studies have confirmed that tear film stability impacts ocular aberrations (Thibos and Hong, 1999; Tutt et al, 2000; Koh et al, 2002; Koh et al, 2008; Montés-Micó et al, 2004; Montés-Micó et al, 2005) using a variety of measurement techniques (e.g., double-pass optical method (Albarran et al, 1997; Montés-Micó et al, 2005; Diaz-Douton et al, 2006), Hartmann-Shack aberrometer (Montés-Micó et al, 2004; Thibos and Hong, 1999; Koh et al, 2002; Diaz-Douton et al, 2006; Koh et al, 2008), contrast sensitivity and vessel contrast measurements (Tutt et al 2000), retro-illumination of the tear film (Liu et al, 2010), videokeratography (Goto et al, 2002), and the Pentacam with fluorescein (Zhuang et al, 2010).

While these surrogate markers for functional loss have shown sensitivity and specificity to dry eye disease, their inability to simultaneously measure tear break-up both objectively and subjectively means that the clinical significance of their findings is hard to quantify. For example, the Objective Scatter Index (OSI) from the Optical Quality Analysis System (OQAS™) (Visiometrics S. L., Ctra. N-150 Km 14.5, Mòdul TR20-IPCT E-08227 Terrassa, Spain) evaluates the amount of light in the outside of a double-pass image in relation to the amount of light in the centre of a double-pass image. The higher the OSI value, the greater the scatter. Without an understanding of how an observed OSI value relates to functional performance (e.g., visual acuity) this represents an arbitrary measure of optical quality which cannot be translated into an endpoint which is clinically meaningful to either physicians or patients.

Consequently, there is a need for instruments and diagnostic methods that can more accurately measure, in real time, optical aberrations in the eye of a patient and their functional consequences. This will allow physicians to interpret the impact of the particular optical aberrations a patient is experiencing in his or her eye in terms of their functional consequences for that patient and can then help guide the physician's choice of an appropriate level of treatment.

The present invention satisfies this need by providing instrumentation and protocols for simultaneously evaluating the relationship between metrics of optical quality in the eye of a patient obtained from double pass images, psychophysical measures of visual performance, and a retro-illumination image of the tear film. The addition of the retro-illumination image in the present instrument enables one to not only map the location of a tear break-up (e.g., central versus peripheral) in a patient's eye, but to also correlate the location of a tear break-up with any changes in optical quality and visual performance. By providing simultaneous measurement of these parameters in real-time, the present instrument reduces or eliminates variability, which can occur when measurements are taken between eye blinks or at separate points in time. Accordingly, the present instrument enables the operator to assess a patient's visual quality more accurately than previously possible.

DEFINITIONS

The term "simultaneously" means occurring at the same time, coincident, coinstantaneous, concomitant.

As used herein, the term "diagnose" means the process of attempting to determine and/or identify a possible disease or disorder and the opinion reached by this process.

As used herein, the term "tear film instability" refers to the observation that the tear film in the human eye is fluctuating in one of several dimensions which can impact optical quality (e.g., thickness).

As used herein, the term "optical quality" refers to the ability of the optics of the eye to bring an image into focus at the retina. The optical quality of the eye can be adversely affected by instability of the tear film and by refractive or other optical aberrations of the eye (Thibos et al. (1999) *Optometry and Vision Science* 76(12):817-825: Albarran et al. (1997) *Contact Lens and Anterior Eye* 20(4):129-135).

As used herein the term "monochromatic" means consisting of radiation of a single wavelength.

As used herein, "infrared light" means light having a wavelength of 700 nm to 1 mm. "Near infrared" light is considered herein to mean light having a wavelength of 700 nm to 1400 nm. "Short-wavelength infrared" light is considered herein to mean light of between 1400 nm and 3000 nm. "Long-wavelength infrared" light is considered herein to mean light of 3000 nm to 1 mm.

As used herein "visible light" means light having a wavelength of 380 nm to 760 nm.

Figure 2:
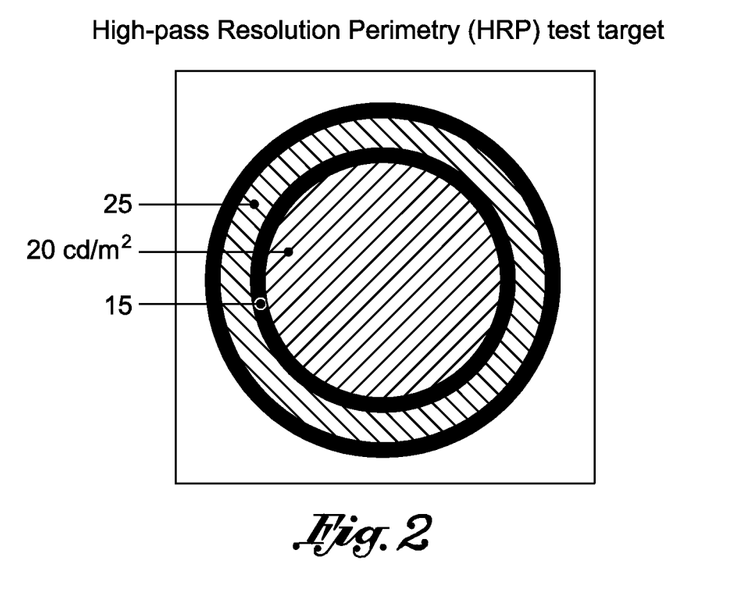
FIG. 2 shows a High-pass Resolution Perimetry (HRP) test target, designed to have a single detection/resolution threshold secondary to the design of the test target. The HRP test target consists of three concentric rings whose average luminance is equal to the background luminance of the screen. The luminance, or luminous intensity, of each ring is shown in candela/square meter.
Figure 3:
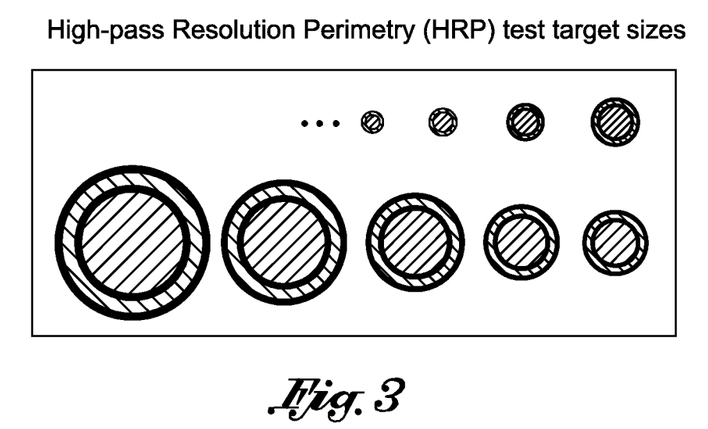
FIG. 3 shows a series of different sizes of HRP targets, differing by 0.1 of a logarithmic unit (1 decibel, dB), for determining a subject's detection threshold.

"High-pass resolution perimetry (HRP)" test targets, also known as "ring" perimetry targets have been described by Frisen (1993) *Documenta Ophthalmologica* 83:1-25. As shown in FIG. 2, an HRP target consists of three rings. The middle ring forms a bright circular core surrounded by inner and outer rings with darker borders. The dimensions and luminances of the rings are calculated to make the target invisibly melt into the background if unresolved. A subject's detection threshold is determined using a series of different sized HRP targets, as schematically shown in FIG. 3. Once the detection threshold is determined using the instrument of the present invention, a subject is then able to manually adjust the size of the HRP target (using keys or up and down arrow keys on the instrument) to maintain the target as just visible throughout each measurement cycle. For example, if a measurement cycle is to last 19.5 seconds, the subject is instructed to maintain visibility of the test target without blinking for the duration of the 19.5 second trial.

As used herein the term "double-pass image" refers to the recording of images of a point light source projected on the retina after retinal reflection and double-pass through the ocular media. The double-pass technique of retinal imaging for measuring optical aberrations is described in, for example, Artal et al. (1995) *J. Opt. Soc. Am. A*. 12:195-201.

"Optical aberrations" refers to imperfections in the components and materials of the eye that may cause light rays to deviate from the desired path (Lombardo et al. (2010) *J. Cataract Refract Surg* 36:313-331). These deviations may result in blurred images and decreased visual performance. The corneal surface, including the tear film, is the dominating structure in the optical power of the eye and is the main contributor to aberrations in the eye (Lombardo et al. (2010) *J. Cataract Refract Surg* 36:313-331). Optical aberrations may include light scattering by the ocular media and retina, which can also reduce visual performance.

As used herein, the term "tear film break up", "TBU", or "tear break up" relates to the instability of the film of fluid covering the corneal epithelium, spread across the anterior segment of the eye by the action of blinking Tear film thinning or disruption (i.e., tear film instability) may occur locally in particular locations between eye blinks. Tear film instability, and ultimately, tear film break up (TBU) can cause blurry vision by disrupting the refractive surface of the eye. This may lead to reductions in optical quality, depending on where in the tear film the break up or instability occurs. The reduction in optical quality upon TBU is due to the exposure of the corneal epithelium, whose rough uneven surface produces greater light scattering, and therefore greater optical aberrations. The tear film break-up process has a length termed "break up time" (BUT), which can be measured using the slit lamp, fluorescein, and the blue filter. In the instrument of the present invention, shown in FIG. 1, visual performance, tear film instability, and optical quality are assessed simultaneously, by 1) recording refractive aberrations in the eye (using an aberrometer) as correlated with the scattering of a light source, such as a 780 nm laser, and 2) by observing when and where TBU occurs on the cornea of the eye, between eye blinks, as assessed through a series of retroillumination (RI) images of the tear film recorded at constant intervals (e.g., every 0.5 s) throughout the measurement period. The RI images are obtained by the reflection of a second laser, emitting infrared light, such as about 940 nm light, and recorded with a second CCD camera. With the present instrument, the RI images captured by Camera C2 show not only when tear break up occurs but where on the corneal surface tear film break up occurs. In certain embodiments, such as that shown in FIG. 1, the aberrometer component of the present instrument is configured to collect a double pass image of the eye. In certain embodiments of the present invention, the light source of the aberrometer may be a HeNe laser emitting at about 632 nm. In certain embodiments the camera used for recording RI images may be an iris camera. Optionally, a CCD and iris camera may be used together to record RI images of the tear film. In general, the wavelength of light used for the aberrometer channel is different from the wavelength of light used for the RI channel. In general, the light used for monitoring optical aberrations is monochromatic light having a wavelength of between about 600 nm and about 900 nm. In general, the light used for capturing (i.e., monitoring) retroillumination images of the tear film is monochromatic light having a wavelength of between about 700 nm to about 1 mm.

When used to describe visualization of HRP test targets, the terms "detection threshold" and "detection threshold level" refer to the smallest HRP test target that can be seen and resolved. As described by Frisen (1993) *Documenta Ophthalmologica* 83:1-25, HRP targets are either seen and resolved, or invisible. With HRP, target contrast is held constant and stimulus value is varied by varying target size, in steps of 0.1 $\log_{10}$ units. Thus, HRP determines resolution thresholds to the nearest decibel.

When used to describe visualization of non-HRP test targets, such as letters or other objects, "detection threshold" and "detection threshold level" refers, at least in part, to the contrast setting, size, or spatial frequency, etc., at which a letter or object is just recognizable by the subject.

As used herein, the term "subject" is synonymous with person and individual. A subject may be a patient previously diagnosed with or suspected of having dry eye disease, or a patient or person with no known previous diagnosis or medical history of eye disease. Generally, the instant invention of the present invention is designed for use with human subjects to assess the optical quality and visual performance of the human eye.

DETAILED DESCRIPTION OF THE INVENTION

One embodiment of the present invention is an instrument or optical system for more accurately measuring simultaneously and in real time metrics of optical quality obtained from double pass images, psychophysical measures of visual performance, and a retro-illumination image of the tear film.

Figure 1:
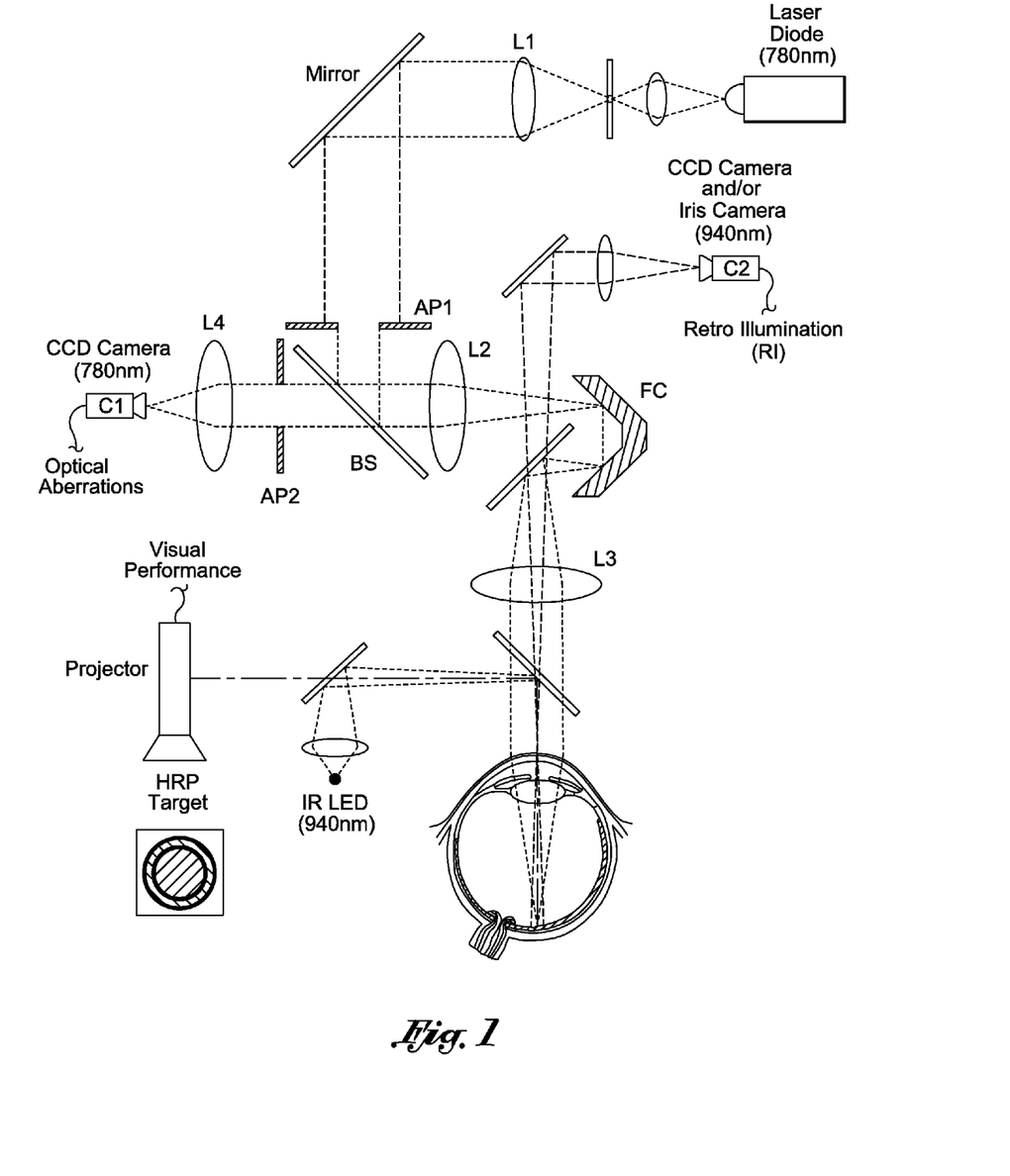
FIG. 1 shows a schematic diagram of an instrument of the present invention, comprising three channels, and configured for the double-pass method of measuring optical aberrations in the eye of a patient, while simultaneously capturing retroillumination images of the tear film, as the patient manually maintains visualization of the HRP test target at the detection threshold. A first computer is connected to camera C2 and to the means for displaying the visual test target (e.g., a projector), while a second computer is connected to camera C1. The first and second computers are synchronized to capture the RI images and light scattering data (optical aberrations) simultaneously, at predefined intervals for a preset period of time, while the patient suppresses eye blinks and manually maintains visualization of the test target at a threshold level by adjusting some dimension, visual feature, or parameter of the target (e.g., size, contrast, brightness or other dimension) using some element connected to the first computer. The element used to adjust a feature, dimension, or parameter of the test target may be up or down arrow keys, a knob, lever, dial, or other like means for precisely or incrementally adjusting a dimension or feature of the target in order to maintain the target at the detection threshold. In certain embodiments of the present instrument, the visual test target is an HRP target, and the subject or patient, maintains visualization of the HRP target at the threshold level by adjusting the size of the HRP target.

As shown in FIG. 1, a double-pass image of the optical aberrations in the human eye starts with a laser diode light source (i.e., 780 nm for the OQAS™) which is filtered and collimated at L1 and AP1. The collimated light is then reflected off a beam splitter (BS) and passes through achromatic doublet lenses L2 and L3 with a focus corrector (FC) positioned between them. The FC can be moved to change the optical distance between L2 and L3 providing a means for spherical correction. The light path from the 780 nm laser diode to the point on the retina constitutes a single pass of the light through the optical system. The light reflecting off the retina then passes back through lenses L3 and L2 and L4 where it is measured by a CCD camera (C1). The light returning to C1 is collimated at aperture AP2. AP2 can be set smaller then the eyes natural pupil to control for variability induced by the natural fluctuation of the iris as light is projected into the eye. In order to center the patient's eye and measure pupil diameter a pupil image can be captured at C2.

Retroillumination (RI) images of the tear film are obtained simultaneously with the double-pass images using a infrared light emitting diode laser. As shown in FIG. 1, an RI image is captured using light from a 940 nm LED, which is directed to the subject's eye using band pass mirrors. The 940 nm light reflected by the subject's eye passes through lens L3, after which it is directed and focused into a CCD camera C2 for detection and image capture by a computer. In certain embodiments the instrument determines the location of a tear film break up using videokeratography. In another embodiment, the instrument determines the location of a tear film break up using the Pentacam with fluorescein method.

The subject maintains visualization of the HRP test target, displayed by a projector, at the detection threshold concurrent with the RI and double-pass imaging, so that visual performance is measured simultaneously with any changes in tear film quality and light scattering (optical aberrations). In certain embodiments, the instrument measures visual performance of the eye using a modified binary search (MOBS) to establish a threshold.

In one embodiment of the invention, synchronized computers are operably connected to Cameras C1 and C2 and to the projector to simultaneously capture RI images and record optical aberrations at predefined intervals for a preset time period while the subject maintains visualization of the HRP test target at the detection threshold. In another embodiment a single computer may be used.

The new instrument of the present invention can be produced from the OQAS™ (Optical Quality Analysis System) developed by Visiometrics S.L. (Terrassa, Spain), by replacing the pupil image camera of the OQAS™ with an Iris Camera (e.g., one capable of detecting infrared light) and adding an Infrared (IR) light source, as shown in FIG. 1. To obtain psychophysical measures of visual performance, the fixation target projector in the OQAS™ can be replaced by a micro-display which is controlled by a second computer. Accordingly, in its final form the instrument of the present invention enables the operator to more accurately measure metrics of optical quality obtained from double pass images, psychophysical measures of visual performance, and a retro-illumination image of the tear film, simultaneously. Moreover, because the optical aberrations and RI images are recorded at multiple intervals over time as tear film instability progresses, the measures can be directly related to the location of tear film break up on the cornea and its possible significance on the individual's visual performance.

Alternatively, the instrument described herein for measuring dry eye disease can be constructed using off-the-shelf components as diagrammed in FIG. 1. Preferably, the wavelength of light used to capture RI images is different from the wavelength of light used to measure optical aberrations.

To obtain psychophysical measures of visual performance, the instrument of the present invention incorporates a third channel, which uses a micro-display controlled by a second computer. The micro-display projects images of test targets, such as HRP targets, which are reflected towards the subject's eye so that the subject may visualize the images. In the case of HRP test stimuli, prior to starting a measurement, the subject is presented with a series of different sized HRP test targets (FIG. 3) to determine the subject's detection threshold. The subject is then asked to maintain the HRP target at the detection threshold throughout the measurement period by adjusting a dimension of the target (e.g., the size of the ring target) up or down using buttons connected to the computer controlling display the HRP target.

In one embodiment of the present invention, double pass images, retro-illumination images of the tear film, and the subject's threshold to a psychophysical stimulus are recorded every 0.5 seconds until a 19.5-second capture sequence has been completed. Thus, there will be 40 images showing optical quality evolution during the 19.5 second time period for both double pass and retro-illumination images. Corresponding to these images are 40 psychophysical threshold estimates. To obtain a psychophysical threshold estimate, the subject's threshold for visualizing a test image is determined before testing begins. Once tear film testing starts the subject adjusts a feature or dimension of the test image (e.g., size, contrast, or spatial frequency) to maintain its visibility at the threshold level throughout the 19.5 second time period.

While visual stimuli varied along many dimensions (e.g., contrast, size, orientation, recognition and displacement) could be envisioned in the device, it has not been recognized within the DED literature that most resolution targets are impractical as clinical diagnostic tools because they typically have two disparate thresholds: one for detection and one for resolution. For example, Lambolt Cs have been employed with the subject identifying the location of the open part of the "C" (i.e., up, down, left, or right). This task requires a subject to first identify a target as seen (detection threshold) and then to identify its orientation (resolution threshold). Each task has its own independent source of error and by definition the latter task has a minimum error rate determined by the number of possible choices: 25% (1 in 4 directions). The utilization of resolution targets and/or staircase threshold measurement techniques means that currently proposed technologies (e.g., Lambolt C's and Visual Acuity letters) will poorly estimate the functional impact of tear film instability (Goto et al, 2002; Johnson et al, 2002).

The current invention can overcome these limitations by employing stimuli (e.g., HRP test targets) which when spatially filtered bring detection and resolution thresholds into coincidence and/or by employing thresholding techniques which are robust to measurement error (e.g., modified binary search (MOBS)).

High-pass spatial frequency filtering can be used to bring a target's detection and resolution thresholds into coincidence (Howland et al, 1978). Taking advantage of this principle, High-pass Resolution Perimetry (HRP) test targets (FIG. 3) were designed to have a single detection/resolution threshold. This is secondary to the design of the test target (FIG. 2) which consists of three concentric rings whose average luminance is equal to the background luminance of the screen. Thus, optical distortion and/or neural under sampling will blur the concentric circles together resulting in an average luminance image equal to the background luminance of the screen (i.e., the rings are blurred into the background and become invisible). HRP uses 14 different sized targets, stepped by 0.1 of a logarithmic unit (1 decibel, dB) to determine a subject's detection threshold (FIG. 3).

HRP was originally designed as a perimetric test for the detection of glaucomatous optic neuropathy (Frisen, 1987; Sample et al, 1992; Martinez et al, 1995). It has not been used for the detection of tear film instability secondary to dry eye disease. The application of this technology to DED has likely not occurred as tests designed for glaucomatous optic neuropathy are usually considered optimized to detect neural loss not optical quality.

Liu et al (2010) built a three channel optical system to simultaneously measure refractive aberrations (Shack-Hartmann aberrometer), 20/40 letter contrast sensitivity (CS), and tear-break up (retro-illumination, RI) (FIG. 3). The optics of this device are an adaptation of a Maxwellian view (Westheimer, 1966; R. Beer D et al, 2005).

Unfortunately, Liu's choice of a stimulus which varies contrast sensitivity (CS) is not optimal for detecting the impact of optical aberration upon functional outcomes. Tear break up causes the Contrast Sensitivity Function (CSF) to shift slightly downward and considerably leftward (i.e., defocus shifts the descending limb leftward) (see Montés-Micó et al, 2005). The left end of the CSF descends rapidly which means that large changes in contrast produce small shifts in the highest spatial frequency (SF) which the optical system can resolve. Conversely small shifts in optical quality will cause significant losses in the highest SF content resolved by the optical system. Thus, the ideal psychophysical stimulus for relating functional outcomes to tear stability and optical aberrations should vary size and/or high spatial frequency content not contrast. The previously proposed technique of utilizing test stimuli, such as High-Pass Resolution Perimetry (HRP) test targets, which when high-pass spatial frequency filtered blend into the background, uniquely satisfy these requirements.

With the present instrument, double pass images, retro-illumination images of the tear film, and the subject's threshold to a psychophysical stimulus are recorded every 0.5 seconds until a 19.5-second capture sequence has been completed. Thus, there will be 40 images showing optical quality evolution during the 19.5 second time period for both double pass and retro-illumination images. Corresponding to these images are 40 psychophysical threshold estimates. To obtain a psychophysical threshold estimate the subject's threshold for visualizing a test image is determined before testing begins. Once tear film testing starts the subject adjusts a dimension of the test image (e.g., size, contrast, or spatial frequency) to maintain its visibility at the threshold level throughout the 19.5 second time period.

The new instrument described herein differs from previous single channel Maxwellian view instruments such as the OQAS™ System in several significant ways: 1) it incorporates three channels; 2) it can simultaneously measure tear break-up both objectively and subjectively; 3) it elucidates the spatial relationship between focal tear film break up (i.e., retro-illumination) and both optical aberrations and psychophysical performance. Thus, this instrument provides an understanding of how optical aberrations relate to functional performance (e.g., visual acuity) and focal disturbances of the tear film throughout a blink-free interval. Furthermore, the use of different sized HRP test targets with the present instrument makes it possible to detect tear film instability secondary to dry eye disease and determine a subject's detection threshold.

In its final form as described above, the instrument uses a three channel optical system which may simultaneously and non-invasively measure refractive aberrations (Shack-Hartmann aberrometer and/or double-pass optical method), psychophysical performance, and tear break-up (retro-illumination, RI). This enables a causal relationship between tear film thickness, optical aberrations and subsequent retinal image quality to be established and significantly reduces testing time and physician/patient burden.

The new device will also significantly increase the reliability of the observed measurements as measurements of objective visual function and tear stability will occur simultaneously and within a single blink-interval (usually less than 10 seconds in patients with DED). This information is currently approximated by completing subjective questionnaires and tear breakup with fuorescein or a non-invasive tear breakup by videokeratography. Together these tests take over 30 minutes of time to complete.

The following examples are intended to illustrate the present invention.

Example 1

A 63 year old female patient tells her ophthalmologist about excess tearing, burning eyes, and intermittent blurred vision. The ophthalmologist conducts an ocular surface exam which includes surface staining assessment with fuorescein/yellow filter, a schirmer I test without anesthetic, and lid and meibomian morphology. The patient is then referred to a technician who utilizes the present invention to simultaneously and non-invasively assess tear film stability and its impact upon functional vision. Thus, a full exam satisfying all of the DEWS (Dry Eye Workshop) recommendations is achieved with two the of critical components (i.e., tear film stability and functional vision) completed by a trained technician. The ophthalmologist determines the patient has DED and provides treatment.

Example 2

Suspected DED patients present to an optometrist complaints of excess tearing, burning eyes, and/or intermittent blurred vision. The optometrist utilizes the present invention to simultaneously and non-invasively assess tear film stability and its impact upon functional vision. The optometrist also utilizes a third channel (i.e., Shack-Hartmann aberrometer and/or double-pass optical method) to screen non-native speaking patients and/or an individual who could not perform the psychophysical task by comparing the Shack-Hartmann aberrometer and/or double-pass optical method of measuring aberrations to the results from a retro-illumination image of the tear film. If tear film instability is identified along with significant impairments in functional vision the patient is referred to an ophthalmologist who conducts an ocular surface exam and provides treatment accordingly.

Example 3

In a clinical trial testing a treatment for DED, the present invention is used to determine effectiveness of the treatment. High-pass Resolution Perimetry (HRP) test targets are substituted with Snellen Visual Acuity optotypes (e.g., letters, "E"s, or symbols) which are varied in size not contrast. This allows direct extrapolation of the test results to established metrics of visual acuity, LogMAR visual acuity, facilitating a clear understanding of the clinical significance of any observed changes in tear break-up.

REFERENCES

1. Albarran C, Pons A M, Lorente A, Montes-Mico R, Artigas J M. Influence of the tear film on optical quality of the eye. Contact Lens Ant Eye. 1997; 20:129-135.
2. Beer D R, MacLeod D I A, Miller T P. The Extended Maxwellian View (BIGMAX): A high-intensity, high-saturation color display for clinical diagnosis and vision research. Behavior Research Methods. 2005; 37: 513-521.
3. Begley C G, Chalmers R L, Mitchell G L, et al. Characterization of ocular surface symptoms from optometric practices in North America. Cornea 2001; 20:610-618.
4. Chen J J, Rao K, Pflugfelder S C. Corneal Epithelial Opacity in Dysfunctional Tear Syndrome. Am J Ophthalmol 2009; 148:376-382.
5. Díaz-Doutón F, Benito A, Pujol J, Arjona M, Güell J L, and Artal P. Comparison of the Retinal Image Quality with a Hartmann-Shack Wavefront Sensor and a Double-Pass Instrument. Invest Ophthalmol Vis Sci. 2006; 47:1710-1716.
6. Frisen L. A computer-graphics visual field screener using high-pass spatial frequency resolution targets and multiple feedback devices. Doc Ophthalmol Proc Ser. 1987; 49:441-446.
7. Goto E, Yagi Y, Matsumoto Y, Tsubota K. Impaired Functional Visual Acuity of Dry Eye Patients. Am J. Ophthalmol. 2002; 133:181-186.
8. Howland B, Ginsburg A, Campbell F. High-pass spatial frequency letters as clinical optotypes. Vision Res 1978; 18:1063-6.
9. Johnson C A, Chauhan B C, Shapiro L R. Properties of Staircase Procedures for Estimating Thresholds in Automated Perimetry. Invest Ophthalmol Vis Sci 1992; 33:2966-2974.
10. Koh S, Maeda N, Kuroda T, et al. Effect of tear film break-up on higher-order aberrations measured with wavefront sensor. Am J. Ophthalmol. 2002; 134:115-117.
11. Koh s, Maeda N, Hirohara Y, Mihashi T, Bessho K, Hori Y, Inoue T., Watanabe H, Fujikado T and Tano Y. Serial Measurements of Higher-Order Aberrations after Blinking in Patients with Dry Eye. Invest Ophthalmol Vis Sci. 2008; 49:133-138.
12. Liu H, Thibos L, Begley C G, and Bradley A. Measurement of the time course of optical quality and visual deterioration during tear break-up. Invest Ophthalmol Vis Sci. 2010; 51:3318-3326.
13. Martinez G A, Sample P A, Weinreb R N. Comparison of high-pass resolution perimetry and standard automated perimetry in glaucoma. Am J Ophthalmol.1995; 119:195-201.
14. Montes-Mico R, Alio J L, Charman N. Postblink changes in the ocular modulation transfer function measured by a double-pass method. J Cataract Refract Surg. 2004; 30:1649-1652.
15. Montés-Micó R, Caliz A, Alio J L. Changes in ocular aberrations after artificial tears instillation in dry eye patients. Invest Ophthalmol Vis Sci. 2005; 46:4468-4473.
16. Montés-Micó R, Phil M. Role of the tear film in the optical quality of the human eye. J Cataract Refract Surg 2007; 33: 1631-1635.

17. Nichols K K, Begley C G, Caffery B, Jones L A. Symptoms of ocular irritation in patients diagnosed with dry eye. Optom Vis Sci 1999; 76:838-844.
18. Ridder W H, J LaMotte, Hall J Q, Sinn R, Nguyenm A L, Abufarie L. Contrast Sensitivity and Tear Layer Aberrometry in Dry Eye Patients. Optom Vis Sci 2009; 86:E1059-E1068.
19. Ridder W H, LaMotte J, Hall J Q, Sinn R, Nguyen A L, Abufarie L. Contrast sensitivity and tear layer aberrometry in dry eye patients. Optom Vis Sci. 2009 September; 86(9): E1059-68.
20. Solomon J A and Pelli D G. The visual filter mediating letter identification. Nature. 2004: 369: 395-398.
21. Sade de Paiva C, Lindsey J L, Pflugfelder S C. Assessing the severity of keratitis sicca with videokeratoscopic indices. Ophthalmology 2003; 110:1102-1109.
22. Sample P A, Ahn D S, Lee P C, Weinreb R N. High-pass resolution perimetry in eyes with ocular hypertension and primary open-angle glaucoma. Am J. Ophthalmol. 1992; 113:309-316.
23. Thibos L N, Hong X. Clinical applications of the Shack-Hartmann aberrometer. Optom Vis Sci 1999; 76:817-825.
24. Tutt R, Bradley A, Begley C, Thibos L N. Optical and visual impact of tear break-up in human eyes. Invest Ophthalmol Vis Sci. 2000; 41:4117-4123.
25. Westheimer, G. (1966). The Maxwellian view. Vision Research, 6, 669-682.
26. Zhuang H, Zhou X, and Xu J. A Novel Method for Pachymetry Mapping of Human Precorneal Tear Film Using Pentacam with Fluorescein. (Invest Ophthalmol Vis Sci. 2010; 51:156-159.

What is claimed is:

1. An instrument for simultaneously monitoring tear film break-up, optical aberrations, and visual performance of an eye of a human subject, the instrument comprising three channels and a first and a second computer,
    (a) the first channel for monitoring optical aberrations in the eye, wherein the first channel comprises:
        (i) a first laser, the first laser emitting a single beam of light having a wavelength of between about 600 nm and about 900 nm;
        (ii) one or more mirrors for directing the beam of light from the first laser to the subject's eye;
        (iii) one or more lenses for focusing the light emitted from the first laser or reflected from the subject's eye;
        (iv) one or more apertures for collimating the light emitted from the first laser or reflected from the subject's eye;
        (v) a first camera capable of detecting the wavelength of light emitted from the first laser;
    (b) the second channel for monitoring tear film break up in the eye, wherein the second channel comprises:
        (i) a second laser, the second laser emitting a single beam of infrared light having a wavelength of between 700 nm to 1 mm;
        (ii) one or more mirrors for directing the beam of light from the second laser to the subject's eye;
        (iii) at least one lens for focusing the beam of light from the second laser;
        (iv) a second camera capable of detecting the wavelength of infrared light emitted by the second laser;
    (c) the third channel for monitoring visual performance, wherein the third channel comprises a means for projecting visual test images onto the eye of the subject;
    (d) the first computer operably connected to the second camera for recording images of the tear film detected by the second camera;
    (e) the second computer operably connected to the first camera, to the means for displaying visual test images, and to an element by which the subject may adjust a feature of a visual test image; and
    (f) the first and second computers synchronized such that optical aberrations and tear film break up can be monitored simultaneously by the first and second cameras and the second computer configured such that the subject can maintain the visual test target at a detection threshold concurrent with the monitoring of tear film break up and optical aberrations.

2. The instrument according to claim 1, wherein the feature of the visual test image that is adjustable by the element is the size, contrast, brightness, or spatial frequency of the test image.

3. The instrument according to claim 1, wherein the means for projecting visual test images onto the eye of the subject is a projector, microprojectori, a micro-display, a cathode ray tube (CRT), or a computer.

4. The instrument according to claim 1, wherein the first and second cameras are charge-coupled device (CCD) cameras.

5. The instrument according to claim 1, wherein the second camera is an iris camera.

6. The instrument according to claim 1, wherein the light emitted by the first laser is monochromatic light, and the light emitted by the second laser is monochromatic light.

7. The instrument according to claim 1, wherein the first camera is configured to capture a double-pass image of the subject's eye.

8. The instrument according to claim 6, wherein the monochromatic light emitted by the first laser has a wavelength of about 780 nm.

9. The instrument according to claim 6, wherein the monochromatic infrared light emitted by the second laser has a wavelength of about 940 nm.

10. The instrument according to claim 6, wherein the monochromatic light emitted by the first laser has a wavelength of about 780 nm and wherein the monochromatic light emitted by the second laser has a wavelength of about 940 nm.

11. The instrument according to claim 1, wherein at least one of the first laser or second laser is a laser diode.

12. The instrument according to claim 1, wherein the visual test images comprise High-pass Resolution Perimetry (HRP) test targets.

13. The instrument according to claim 8, wherein the instrument measures visual performance of the eye using a modified binary search (MOBS) to establish a threshold.

14. The instrument according to claim 1, wherein the instrument determines the location of tear film break up using videokeratography.

15. The instrument according to claim 1, wherein the instrument determines the location of a tear film break up using the Pentacam with fluorescein method.

16. A method for monitoring (x) tear film break-up, (y) optical aberrations, and (z) visual performance of an eye of a human subject simultaneously, the method comprising using the instrument set forth in claim 1 to monitor each of (x), (y), and (z) simultaneously in a human subject, wherein monitoring (x) comprises illuminating the subject's eye with the second laser and collecting one or more images of the second laser light reflected from the subject's eye with the second camera; wherein monitoring (y) comprises illuminating the subject's eye with the first laser and collecting one or more images of the first laser light after a double-pass through the subject's eye with the first camera; and wherein measuring (z) comprises having the subject maintaining visualization of a High-Pass Resolution Perimetry (HRP) test target at a threshold level without blinking, and wherein each of (x), (y), and (z) is monitored simultaneously at predefined intervals for a preset period of time by the first and second computers with no eye blinks between the predefined intervals or during the preset period of time.

17. The method of claim 16, wherein the predefined interval is 0.5 seconds and the preset period of time is 19.5 seconds.

18. The method of claim 16, wherein 40 double-pass images and 40 tear-film break up images are captured in the preset period of time.

* * * * *

UNITED STATES PATENT AND TRADEMARK OFFICE
CERTIFICATE OF CORRECTION

PATENT NO. : 8,909,327 B1
APPLICATION NO. : 13/167099
DATED : December 9, 2014
INVENTOR(S) : Charles Bosworth It is certified that error appears in the above-identified patent and that said Letters Patent is hereby corrected as shown below:

On the Title Page

On page 2, in column 2, item (56) under "Other Publications", line 3, delete "Ophthalmo1." and insert -- Ophthalmol. --, therefor.

On page 2, in column 2, item (56) under "Other Publications", line 10, after "optical" insert -- quality --.

In the Specification

In column 1, line 54, delete "fuorescein" and insert -- fluorescein --, therefor.
In column 2, line 19, delete "fuorescein" and insert -- fluorescein --, therefor.
In column 2, line 20, delete "fuorescein" and insert -- fluorescein --, therefor.
In column 4, line 41, delete "fluroescein," and insert -- fluorescein, --, therefor.
In column 9, line 21, delete "fuorescein" and insert -- fluorescein --, therefor.
In column 9, line 32, delete "fuorescein/" and insert -- fluorescein/ --, therefor.
In column 9, line 39, delete "the of" and insert -- of the --, therefor.

In the Claims

In column 12, line 18, in claim 3, delete "microprojectori," and insert -- microprojector, --, therefor.

Signed and Sealed this
Twenty-first Day of April, 2015

Michelle K. Lee
*Director of the United States Patent and Trademark Office*